United States Patent [19]

Guirguis

[11] Patent Number: 4,953,561
[45] Date of Patent: Sep. 4, 1990

[54] URINE TESTING MODULE AND METHOD OF COLLECTING URINE ANTIGEN

[75] Inventor: Raouf A. Guirguis, Rockville, Md.

[73] Assignee: Cancer Diagnostics, Inc., Rockville, Md.

[21] Appl. No.: 411,041

[22] Filed: Sep. 22, 1989

Related U.S. Application Data

[63] Continuation-in-part of Ser. No. 408,547, Sep. 18, 1989.

[51] Int. Cl.$^5$ ............................................. A61M 5/165
[52] U.S. Cl. .................................. 128/771; 604/318; 422/60
[58] Field of Search ..................... 128/760, 762, 771; 604/318, 404; 422/56, 60

[56] References Cited

U.S. PATENT DOCUMENTS

| | | |
|---|---|---|
| 3,774,455 | 11/1973 | Seidler et al. ...................... 128/771 |
| 4,040,791 | 8/1977 | Kuntz ................................. 128/762 |
| 4,557,274 | 12/1985 | Cawood ............................. 128/760 |
| 4,573,983 | 3/1986 | Annis ................................. 128/760 |
| 4,827,944 | 5/1989 | Nugent .............................. 128/771 |

*Primary Examiner*—Max Hindenburg
*Attorney, Agent, or Firm*—Gipple & Hale

[57] ABSTRACT

An apparatus for testing biological molecular indicators in urine comprising a tubular container, and a sample container holding beads with immobilized ligands. Urine is transported through the tubular container under pressure to flow through the sample container which screens off the antibodies so that antigens of the carried by the urine fluid are collected and concentrated on the beads.

18 Claims, 3 Drawing Sheets

URINE TESTING MODULE AND METHOD OF COLLECTING URINE ANTIGEN

RELATED CASES

This application is a continuation-in-part application of U.S. Pat. Application Ser. No. 07/408,547, filed Sept. 18, 1989, pending.

BACKGROUND OF THE INVENTION

The present invention is directed to medical and laboratory fluid specimen collecting and testing apparatus, and more specifically to an apparatus for detecting the presence of specific antigens in biological fluids.

The family of immunoassay works upon the simple principle that is the specific recognition of an antigen by an antibody. Thus specific antigen detection and quantification requires an antibody which recognizes the uniqueness of an antigen. The antigen binding site of antibodies recognizes about six amino acids or their equivalent in mass. One unique binding site serves as an identifying marker for that protein.

When a definitive antibody for a given antigen is available it is used to identify the antigen in the sample mixture. Once the antibody combines with the antigen a means is needed to recognize the complex. There presently exists a need to concentrate antigens from volumes of fluid when the antigen is not present in measurable quantities in specific fluid volumes.

The present invention is directed toward an apparatus and a method which can use immunoassay in sample treatment apparatus for diagnostic and testing purposes of specific urine antigen by concentrating the specific urine antigen in a small volume area.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. While urine is commonly collected in 100 ml containers the actual urine testing is commonly conducted with relatively small amounts of sample around 0.2–0.5 ml in volume. Thus because of the small test quantity, cancer producing antigen can only be ascertained after the cancer is in an advanced or late tumor stage. The rest of the urine sample is used for further testing or is thrown away. Additional problems occur in shipment when dealing with urine because of the relatively large volume of fluid involved in the collection specimen sample. There is also the risk of sample deterioration because of the relatively short sample shelf life of urine unless kept in specific temperature conditions. In addition there is also the potential for specimen damage or spillage during the collection and/or shipment process as well as the potential for destruction of certain molecular components of the specimen such as antigens contained therein, because the packaging does not protect the urine or causes chemical changes of different fluid components which will negate the test results or result in false data being obtained when the specimen is tested.

There currently exists a need to concentrate molecular components of biological fluids for the presence of cancer at an early stage in the development of the cancer.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

Another specimen collection device shown by U.S. Pat. No. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle disposable apparatus and method which transports a fluid sample such as urine through a specific immobilized antibody bead bed to capture a concentrated amount of antigen materials from the urine allowing more sensitive cancer detection from the sample while also providing that the test specimen can be compactly stored for a period of time in concentrated form allowing cancer testing to be performed quickly and accurately by distal testing facilities with minimum elapse of time.

BRIEF SUMMARY OF THE INVENTION

The invention is directed toward a urine antigen collection device. This device is in the form of a removable stackable sealed urine antigen sample container having an interior chamber with primary antibody covalently bound to beads. The urine is pumped through the container where it engages and passes through a filter having a 5 micron filter particle size which screens out cells and cell debris but allows passage of filtered urine fluid and antigen through an antibody bead bed. The beads in the bead bed have specific antibodies covalently bound thereto to capture specific antigen carried by the urine fluid. The urine can be buffered to a pH of 7.8 so that it remains in a stable preserved state. If there is an absence of the antigen in the specimen sample the antibody will remain unoccupied and render a negative test result.

It is thus an object of the invention, particularly where ligands such as antigens are being removed from the body fluids for testing to collect and concentrate specific antigens from the body fluid samples. Previously such testing has been accomplished by a series of tests involving a number of different containers and expensive laboratory equipment of a limited sensitivity.

In the accompanying drawings, there is shown an illustrative embodiment of the invention from which these and other of objectives, novel features and advantages will be readily apparent.

DETAILED DESCRIPTION OF THE INVENTION

Figure 1:
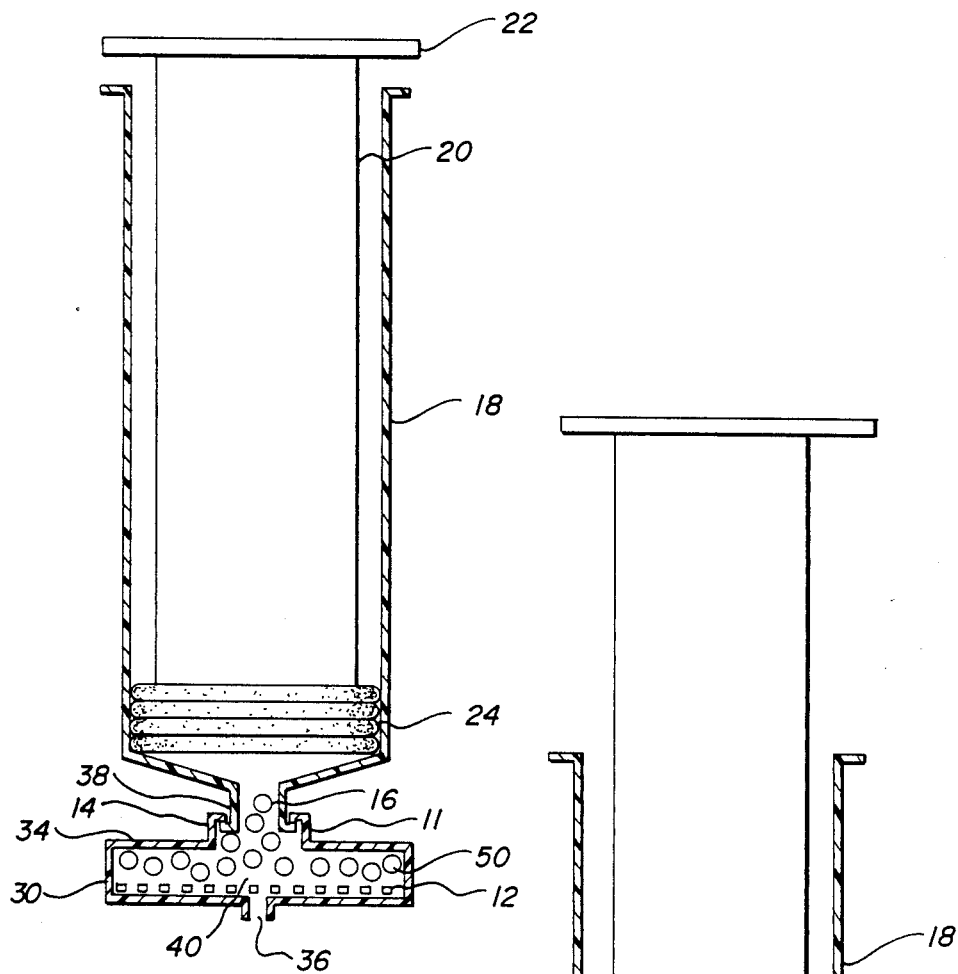
FIG. 1 is a cross sectional schematic view of the inventive urine testing device.
Figure 2:
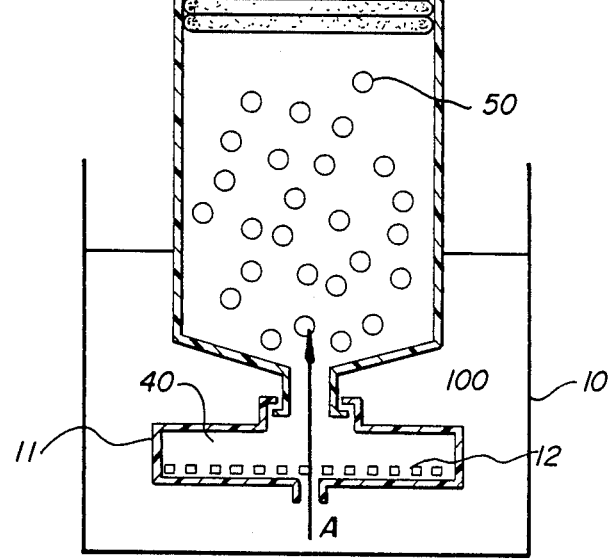
FIG. 2 is a cross sectional schematic view of the invention of figure 1 showing the urine test container immersed in urine with urine entering the syringe with direction of movement shown by arrow A.
Figure 3:
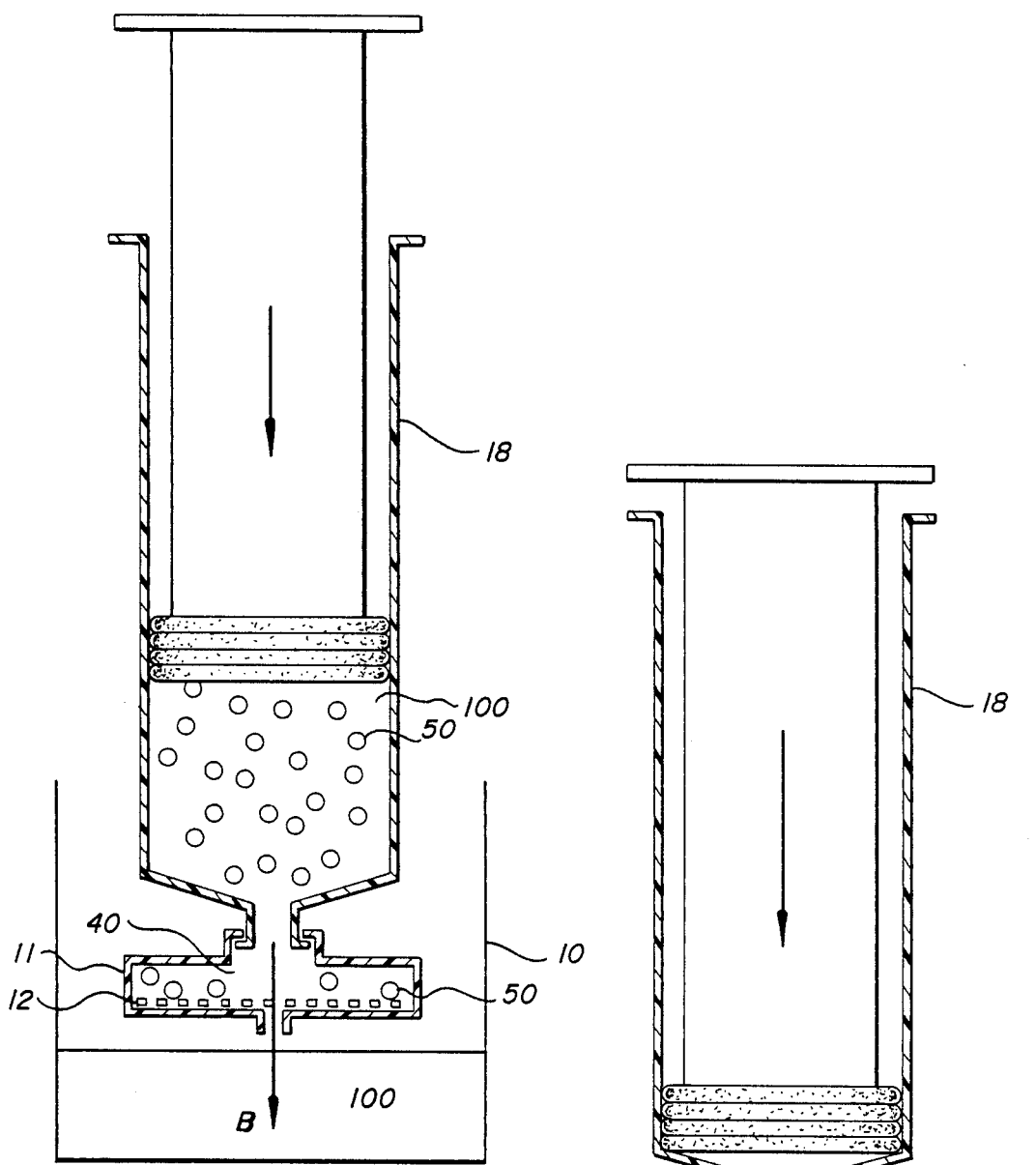
FIG. 3 is a cross sectional schematic view of the invention of FIG. 1 showing sequential movement of the syringe plunger from that shown in FIG. 2 with urine being discharged from the syringe with direction of movement shown by arrow B and the immobilized antibody beads piled upon the container filter.
Figure 4:
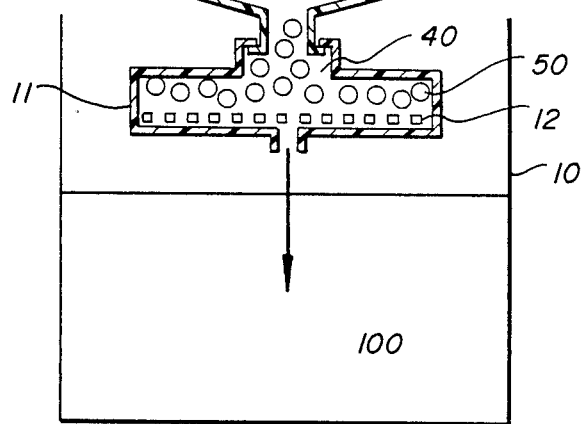
FIG. 4 is cross sectional schematic view of the syringe plunger shown in FIG. 3 after the urine has been fully discharged from the syringe and beads carrying specific antigen have been deposited in the container.

The preferred embodiment and best mode of the invention is seen in FIGS. 1 through 5. The initial collection of the urine is normally housed in a graduated 100 ml container 10. Such a container is currently manufactured by Becton Dickinson Labware under the designation 4013 specimen container. This collection container holds 4.5 oz. (approx. 133 ml) and is graduated with a polyethylene snap lid. The invention as shown in the drawings comprises a beads container 11 with treatment filter 12 mounted therein. The filter 12 preferably has a filter particle size of 5 microns but can range from 1-5 microns or any size which is suitable to allow fluid flow with antigens to pass therethrough but also prevent the passage of beads 50. The beads sample container 11 can be a disposable sterile single use filter assembly manufactured by Gelman Sciences under the trademark ACRODISC with a 5 VM filter. However, any suitable filter can be used such as the aqueous glass microfiber filter manufactured by Xydex, a subsidiary of Genex Corporation or a membrane member manufactured by Millipore Corporation. One end 14 of the container is fitted with a threaded projection which is adapted to fit onto the luer lock 16 of a 30 cc syringe 18, manufactured by Becton Dickinson & Co. It should be noted that any pump type device could be used in place of the syringe as for example an autovial spunglass filter manufactured by Genex Corporation. The syringe 18 has a barrel 20, piston 22 and piston head 24. While the invention can be used for any body fluid it is primarily designed for use in collecting concentrated urine antigen samples for use in testing for the presence of various kinds of cancer in the body to determine the presence and stage of the cancer.

As shown in FIGS. 1 through 5 a beads sample container 11 is constructed of polystyrene. The container housing has an exterior cylindrical wall 30 with end walls 32 and 34 respectively defining a urine entrance port 36 and exit port 38. The chamber 40 of the beads sample container 11 contains a filter 12 with a filter size ranging from 0.5 to 5 microns mounted at one end and a bed of beads 50 with immobilized antibodies positioned on the syringe side of the filter.

The bead 50 are preferably visible (above 10 micron in diameter) so that their flow into the syringe and back to the container can be visually observed to make sure of maximum bead contact with the urine. Antibodies are immobilized (covalently bound) on beads 50 as is well known in the art and are designed to have binding sites which have a high affinity for the epitopes of the cancer antigens carried in the urine.

It should be noted that the volume of beads 50 is important and the beads should not be greater then the volume of the container chamber 40 so that the syringe neck will not become jammed.

The principle of affinity chromatography requires that a successful separation of a biospecific ligand is available and that it can be chemically immobilized to a chromatographic bed material, the matrix. Numbers of methods well known in the art have been used to couple or immobilize antibodies to a variety of activated resins. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

An advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10-100 cm/min).

The resin bead material 50 with matrix and primary ligand (in this case immobilized antibody) having had flow contact with the filtered urine in buffered form from the addition of 10 ml of 200 mM Tris buffer pH 7.8 manufactured by Pharmacia captures through antigen-antibody reaction or immune reaction the specific ligand component carried by the urine namely, the non complexed antigen. This buffering agent adjusts the urine pH. The buffer solution can be added to the collection container 10 by directly adding it from the syringe 18 prior to withdrawing the urine into the syringe or simply adding it from another container. When the specific antigen is present in the urine testing sample 100 the antigen reacts with the antibody to form antigen-antibody complexes. The complexed antigen-antibody carried by beads 50 remains in the housing chamber 30 as is clearly shown in FIG. 4. If there is an absence of the antigen in the specimen sample 100 the antibody will remain unoccupied.

Testing is presently done by using 0.2-0.5 ml aliquots of urine. The present high affinity beads 50 can capture the antigen present in 100 ml or even more of the sample, depending on the frequency of filling and emptying the syringe 18. This will result in 500× fold increase in the amount of antigen being captured by the beads. Preferably the syringe is filled with urine allowing the beads to move freely into the barrel of the syringe for maximum fluid contact and mixing. The syringe is emptied and refilled a number of times for maximum concentration so that 1,000× antigen concentrations from that previously obtainable can be obtained.

The container 11 is removed from luer lock 16 of syringe 18 and ports 36 and 38 are closed with screw or snap fit caps 37 to provide a container filled with concentrated specimen sample that be stacked (mate male end 32 into female end 34) and shipped. Furthermore the specimen life of the buffered specimen is 6 months or longer under ordinary storage conditions after washing the beads with preservative solution e.g. 0.01% Sodium Agide (Bacteriostatic agents).

Upon receipt of the specimens the container is placed on a syringe containing an eluting buffer which release the antigens from the antibody on the beads providing a concentrated antigen sample for testing purpose.

Figure 6:
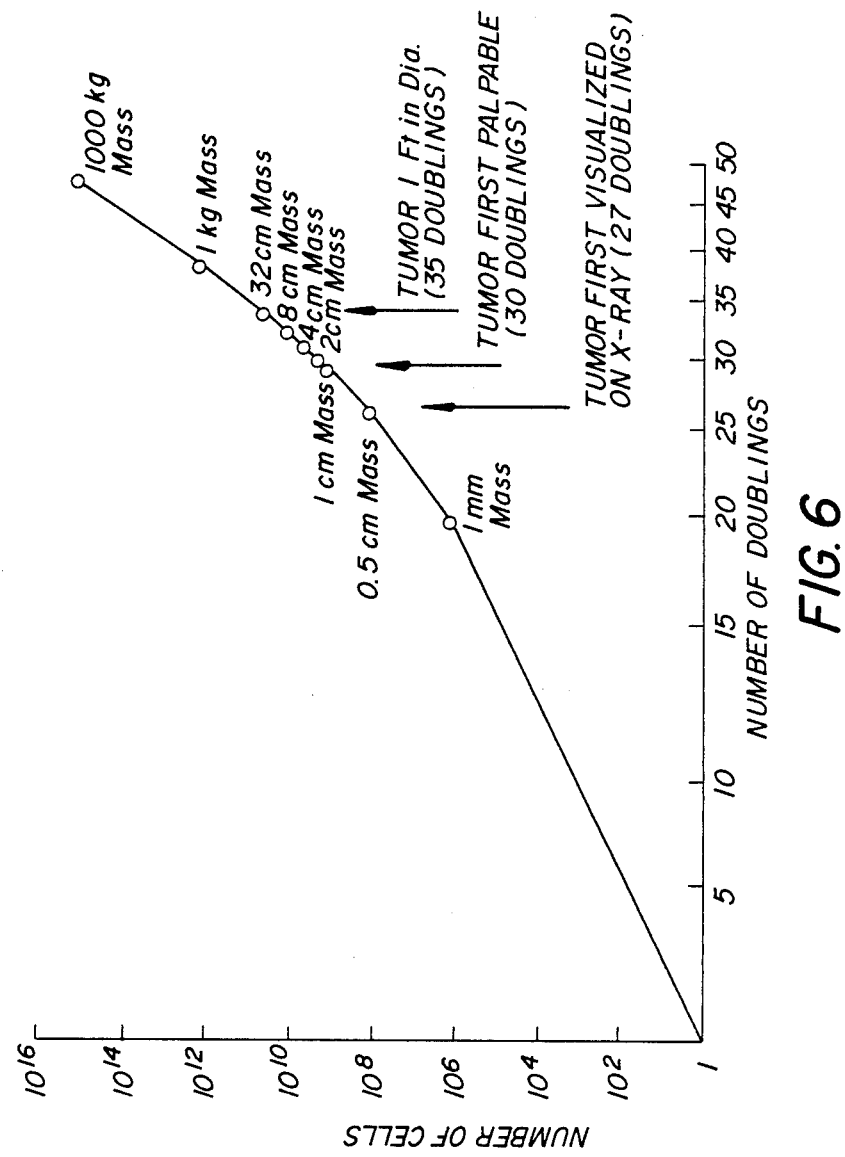
FIG. 6 shows a schematic graph showing tumor load development in correlational with diagnosis and treatment time.
Figure 5:
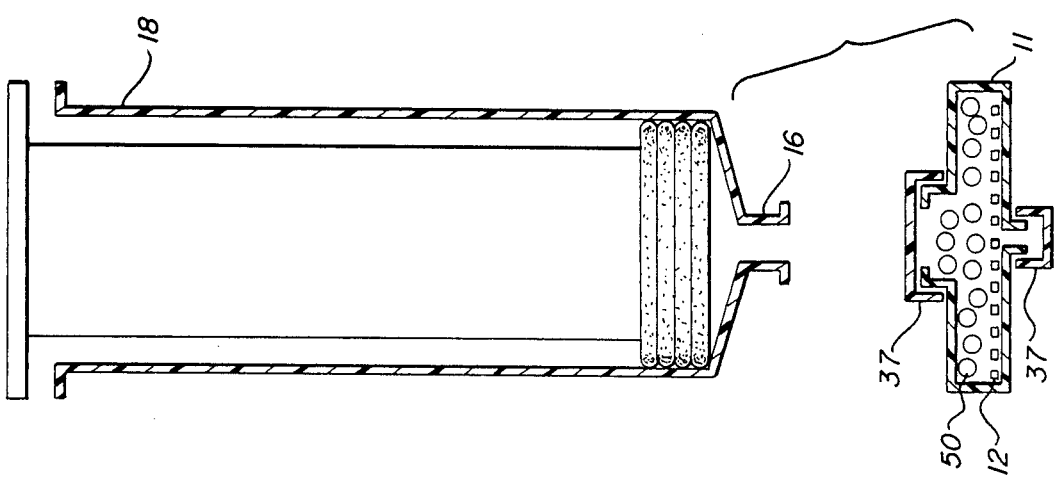
FIG. 5 is an exploded cross sectional schematic view showing removal of the testing container after removal from the syringe.

As can be seen from the graph of FIG. 6 this antigen concentration apparatus and method allows for the first time the detection of the early stages of cancer as compared with present day testing which can only identify the later tumor stage. Thus the physician now has available the capability of quick testing for cancer patients after surgery or for the testing of patients with suspected cancer.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for testing molecular specimens in a biological fluid comprising a syringe, a specimen treatment unit mounted to said syringe, said specimen treatment unit comprising means comprising a housing with an inlet and outlet means, a filter means mounted to said housing which allows fluid flow and antigens carried by said biological fluid to flow there through, a primary antibody bead means contained in said housing on the syringe side of said filter means which is adapted to capture designated antigens carried by said fluid.

2. An apparatus for testing molecular specimens in a biological fluid as claimed in claim 1 wherein said housing filter comprises a porous membrane means with no less than 2 micron pore size to prevent flow of antibodies through said membrane means.

3. An apparatus for testing molecular specimens in a biological fluid as claimed in claim 1 wherein said specimen treatment unit to removably mounted in said syringe.

4. An apparatus for testing molecular specimens in a biological fluid as claimed in claim 1 wherein said specimen treatment unit is fixedly secured to said syringe.

5. An apparatus for collecting molecular specimens from a urine sample comprising a tubular container; a specimen collection unit removably mounted to said tubular container, said specimen collection unit comprising a housing defining at least one chamber bead means with covalently bound antibody means positioned in one of said at least one chambers for the capture of specified antigen carried in urine; and a filter means housed in said specimen collection unit housing to prevent flow of bead means with covalently bonded antibody means carried by said urine into said urine sample while allowing flow of said bead means into said tubular container.

6. An apparatus as claimed in claim 5 wherein said bead means is provided with color means to create a visual color indicator.

7. An apparatus as claimed in claim 5 wherein said tubular container is a syringe with a lure lock and said housing has attachment means adapted to be secured to said lure lock.

8. An apparatus as claimed in claim 7 wherein said syringe contains a buffering solution.

9. An apparatus as claimed in claim 8 wherein said buffering solution is M Tris buffer.

10. An apparatus as claimed in claim. 8 wherein at least 200 ml of buffering solution is contained in said syringe.

11. An apparatus for testing molecular specimens in a biological fluid comprising a pump means, a specimen treatment unit mounted to said pump means, said specimen treatment unit comprising means comprising a housing with an inlet and outlet means, a filter means mounted to said housing which allows fluid flow and antigens carried by said biological fluid to flow therethrough, a primary antibody bead means contained in said housing on the pump means side of said filter means which is adapted to be carried and capture designated antigens carried by said fluid through said outlet means into said pump means.

12. A method of testing for predetermined molecular bodies in a urine specimen comprising the steps of:
  a. collecting urine into an apparatus for collecting biological fluids;
  b. passing the urine through a urine treatment container connected to an elongated tubular apparatus holding an immobilized antibody bead means, to contact the bead means and a filter member also positioned in the housing which prevents the flow of bead means to the urine collection apparatus while permitting the flow of bead means into the elongated tubular apparatus; and
  c. removing the urine treatment container from the tubular apparatus with the immobilized antibody bead means contained therein along with designated captured antigen from the urine; and
  d. testing the immobilized antibody bead means with designated captured antigen to obtain a cancer indicator test result.

13. A method of testing for predetermined antigen in urine comprising the steps of:
  a. mounting a removable test container means on a fluid collecting apparatus, said test container means comprising a housing with a filter and immobilized antibody bead means;
  b. placing the fluid collecting apparatus in fluid communication with urine and causing the urine to flow through the test container means in one direction and engage said antibody bead means depositing antigens carried in the urine on antibodies immobilized on the bead means,
  c. transporting said urine to flow through the test container means in the opposite direction depositing antibody bead means carried in the test container means housing; and
  d. removing the test container means from said fluid collecting apparatus.

14. The method as claimed in claim 13 including repeating steps b and c at least one time.

15. The method as claimed in claim 13 including repeating steps b and c a plurality of times.

16. The method as claimed in claim 13 including the step of mixing said urine with a buffering solution before removing the test container means from said fluid collecting apparatus.

17. A method of collecting antigen from urine for testing for cancer comprising the steps of:
   a. mixing a buffer solution in urine;
   b. withdrawing the buffered urine into a syringe means containing a filter and beads with immobilized antibodies;
   c. capturing antigen from the buffered urine onto the beads with immobilized antibodies;
   d. discharging the urine in the syringe means through the filter collecting the beads in a centralized area; and
   e. removing the beads for testing for the presence of cancer.

18. The method as claimed in claim 17 including the further step of eluting the beads to release the antigens from the antibodies.

* * * * *